United States Patent [19]

Steür et al.

[11] Patent Number: 5,060,635

[45] Date of Patent: Oct. 29, 1991

[54] INTERNAL FIXATION KIT

[75] Inventors: Gerhard Steür; Günther Sauer, both of Berlin, Fed. Rep. of Germany

[73] Assignee: Mecron medizinische Produkte GmbH, Berlin, Fed. Rep. of Germany

[21] Appl. No.: 410,063

[22] Filed: Sep. 19, 1989

[30] Foreign Application Priority Data

Sep. 21, 1988 [DE] Fed. Rep. of Germany ... 8812077[U]
Jan. 2, 1989 [DE] Fed. Rep. of Germany ... 890080[U]

[51] Int. Cl.$^5$ .......................... A61F 5/00; A61F 2/28; A61F 2/44
[52] U.S. Cl. ...................................... 128/69; 606/61; 623/16; 623/17
[58] Field of Search ............... 128/69; 606/61; 623/17, 623/16

[56] References Cited

FOREIGN PATENT DOCUMENTS 1943801 1/1972 Fed. Rep. of Germany .
2621384 11/1977 Fed. Rep. of Germany .
2810129 9/1978 Fed. Rep. of Germany .
3241589 5/1984 Fed. Rep. of Germany .

Primary Examiner—V. Millin
Attorney, Agent, or Firm—Spencer & Frank

[57] ABSTRACT

A device which includes an elongated rod made of a metal having a generally silver color and having a threaded end and a component having an internal thread which engages the end of the rod. The threaded end portion has a borderline where a region coated with titanium nitride borders an uncoated region of the rod.

11 Claims, 1 Drawing Sheet

INTERNAL FIXATION KIT

CROSS REFERENCE TO RELATED APPLICATION

This application claims the priority of Applications Ser. No. G 8812077.5, filed Sept. 21, 1988, and Ser. No. G 8900080.3, filed Jan. 2, 1989, in the Federal Republic of Germany, the subject matter of which is incorporated herein by reference.

BACKGROUND OF THE INVENTION

The invention relates to a kit for an internal fixing device, particularly for the fixation of vertebrae, which includes a counterclockwise thread and/or a clockwise thread.

Such fixing devices serve primarily for the internal fixation of defects in the thoracic and lumbar parts of the spine.

Due to their small size, the implantation of conventional fixing devices requires a high degree of skill and experience on the part of the implanting surgeon. Under surgery conditions, in particular, it is difficult to determine whether the parts of the kit or the threaded connections on these parts have counterclockwise or clockwise threads. Differentiation between a clockwise thread region and a counterclockwise thread region can often only be made by experimentally screwing on the screw cap.

To ensure sufficient stressability for the fixing device it is also necessary that the regions provided with external threads are screwed in to a minimum depth. Such depth, however, cannot be estimated since the total length of the external threads differs. However, when such a fixing device is set for the patient, knowledge of the minimum screw-in depth required is absolutely necessary, so that the element provided with the external thread will not inadvertently separate from the corresponding element provided with an internal thread and thus endanger the fixation.

Since the surfaces of known implants are configured uniformly with respect to their optical reflection properties, there are no regions which could serve as identification.

SUMMARY OF THE INVENTION

It is the object of the invention to provide a fixing device of the above-mentioned type which is provided with a coating that differs with respect to its optical characteristics, particularly the reflection effect of its non-coated regions but nevertheless has good biocompatibility, it being possible, in particular, to contrastingly coat larger areas as well.

This is accomplished by a device which includes a metal elongated rod having a threaded end and a component or nut having an internal thread which engages the end of the rod. The threaded end portion has a borderline where a region coated with the titanium nitride borders and uncoated region of the rod which is silver in color. In a preferred embodiment, both ends of the rod have a coated region. Additionally, the size of the coated regions may be different for the two ends.

Coatings of titanium nitride are known in principle for implants intended for surgical bone treatments, as disclosed, for example, in German Patent No. 1,943,801.

The invention is based on the realization that, due to their golden color which differs from the remaining silver-colored material, TiN coatings produce a contrast by which various functional regions of components of the kit can be distinguished for a long time and, in a way that is compatible with the human body, when the coated regions exist next to non-coated regions and consequently, are contrastingly distinguishable therefrom. The coating according to the invention is particularly favorable in this connection since it permits the contrasting treatment of larger surface regions as well.

Since TiN layers appear as a gold color, they are clearly distinguishable, even under surgery conditions, from the steel-gray of the remaining components of the kit which are made of high-grade steel or titanium alloys. Another advantage of the TiN coating is its excellent biocompatibility. It has been found that TiN coated high-grade steel implants exhibit a better affinity index after six weeks of implantation than uncoated high-grade steel implants (K. Hayashi, et al, "The Screening Of Metal Implants Coated With Several Types Of Ceramics," The Third Biomaterial Congress; Apr. 21–25, 1988; Icyotot; Japan). Moreover, TiN coated high-grade steel implants have greater corrosion resistance than uncoated implants.

Advantageous features of the invention are described in greater detail below together with a description of the preferred embodiment of the invention and reference to the drawing figures.

DETAILED DESCRIPTION OF THE PREFERRED EMBODIMENT

Figure 3:
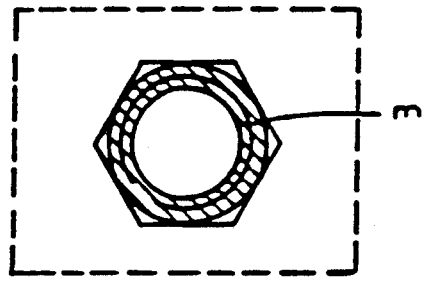
FIGS. 2 and 3, two components adapted to the first component and equipped with internal threads.
Figure 1:
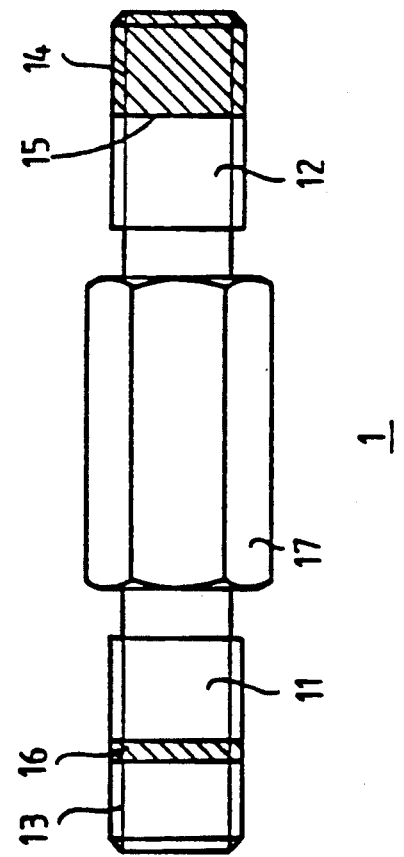
FIG. 1, a side view of a component of the kit according to the invention equipped with an external thread for a fixing device.
Figure 2:
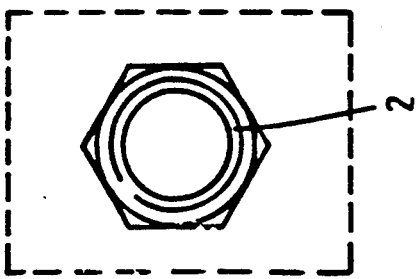

The embodiment of a kit shown in FIGS. 1 to 3 includes an adjustment member 1 provided with external threads which engage in two components 2 and 3 provided with internal threads as shown in FIGS. 2 and 3. The latter components themselves can be connected, by means of projections, engaging means or additional components shown only schematically in dashed lines in the drawing, with the parts of the human skeleton to be secured, particularly with vertebrae or bone fragments.

Adjustment member 1 is provided with two threaded rods 11 and 12 which are each provided with a counterclockwise thread 13 and a clockwise thread 14, respectively. In the embodiment shown in the drawing, the threaded rod on the left has a counterclockwise thread and the threaded rod on the right has a clockwise thread. The same applies for the associated components 2 and 3 shown in FIGS. 2 and 3.

Between threaded rods 11 and 12 there is disposed a hexagonal actuating member 17 which can be adjusted by means of a wrench so that the two threaded rods 11 and 12 can be screwed into the internal threads of components 2 and 3. By changing the position of the hexagon, it is thus possible to set the relative distance between components 2 and 3.

Expediently, the two screw components 2 and 3 are screwed onto the respective external threads 13 and 14, respectively, of adjustment member 1 to about half the possible distance before the fixing device is implanted.

The high-grade steel regions of fixing device components 1 to 3 which are coated with titanium nitride are shown in hatching in the drawing. The outer region 14 of the threaded rod is coated with TiN, with this coating ending below the middle of the threaded region. A borderline 15 between the region coated with titanium nitride and the uncoated region extends tangentially in the form of a ring around the threaded rod. The opposite component provided with the counterclockwise thread (threaded rod 11) is provided with a coating of TiN in the form of a ring 16.

This ring extends from the outer end of threaded rod 11 at a distance which corresponds to the distance of edge 15 of the solid coating 14 on threaded rod 12. With this type of marking, the surgeon, when making the adjustment, is able to detect inevitably and without any mental effort, due to the appearance of the gold-colored region, that he must not continue unscrewing the threads, i.e. turning the hexagon 17 to move components 2 and 3 away from one another, since otherwise the danger would arise that threaded rod 11 or 12, could come out of the corresponding partner.

At the same time, the coatings differ on the clockwise and counterclockwise threads, with the exterior portion of threaded rod 12 being coated completely with a layer of titanium nitride. This is also true correspondingly for component 3 with respect to its region to be screwed onto threaded rod 12 (hatching in the drawing). Here, too, the surgeon will be able to join the associated components without much mental effort so that the process of assembling the fixing device under surgery conditions is accelerated and false attempts are excluded from the start.

The coated, contrasting regions of the implants differ clearly from untreated regions with respect to their surface reflection characteristics and thus make possible good optical distinction.

The present invention is not limited in its embodiments to the above-described preferred embodiment. Rather, a number of variations are conceivable which take advantage of the described solution even for basically different configurations.

What is claimed is:

1. An internal fixation device comprising:
   an elongated member comprising metal having a generally silver color and including a first end portion, said first end portion having an external thread and having a region coated with titanium nitride which borders an uncoated region at a first borderline; and
   a first component having an internal thread for engaging said external thread on said first end portion, said coated region on said first end portion being axially so located as to be visible prior to said first end portion disengaging from said first component when said elongated member is rotated in a direction which causes said first component to move outwardly relative to said first end portion.

2. The device of claim 1 wherein said elongated member further includes:
   a second end portion having an external thread and a region coated with titanium nitride which borders an uncoated region at a second borderline; and
   a second component having an internal thread for engaging said external thread on said second end portion, said coated region on said second end portion being axially so located as to be visible prior to said second end portion disengaging from said second component when said elongated member is rotated in a direction which causes said second component to move outwardly relative to said second end portion.

3. The device of claim 2, wherein said coated regions are gold-colored.

4. The device of claim 2, wherein said coated region of said first end portion is axially longer than said coated region of said second end portion.

5. The device of claim 2, wherein said first end portion has a clockwise thread and said second end portion has a counterclockwise thread.

6. The device of claim 2, wherein one of said coated regions is ring-shaped.

7. The device of claim 2, wherein said internal thread of one of said components has a titanium nitride coating.

8. The device of claim 1, wherein said elongated member includes a middle portion having a hexagonal cross-section for allowing said elongated member to be gripped and turned, said hexagonal portion being located between said two end portions.

9. The device of claim 1, wherein said elongated member comprises steel.

10. The device of claim 1, wherein said elongated member comprises titanium.

11. The device of claim 1, wherein said coated region of said first end portion is gold-colored.

* * * * *